US011717663B2

(12) United States Patent
Gill et al.

(10) Patent No.: US 11,717,663 B2
(45) Date of Patent: Aug. 8, 2023

(54) NEUROLOGICAL APPARATUS COMPRISING A PERCUTANEOUS ACCESS DEVICE

(71) Applicant: RENISHAW (IRELAND) LIMITED, Swords (IE)

(72) Inventors: Steven Streatfield Gill, Bristol (GB); Paul David Fielder, Gloucestershire (GB)

(73) Assignee: RENISHAW (IRELAND) LIMITED, Wotton-under-Edge (GB)

( * ) Notice: Subject to any disclaimer, the term of this patent is extended or adjusted under 35 U.S.C. 154(b) by 297 days.

(21) Appl. No.: 16/998,491

(22) Filed: Aug. 20, 2020

(65) Prior Publication Data

US 2020/0376252 A1 Dec. 3, 2020

Related U.S. Application Data

(63) Continuation of application No. 14/581,549, filed on Dec. 23, 2014, now Pat. No. 10,751,520, which is a
(Continued)

(30) Foreign Application Priority Data

Nov. 23, 2006 (GB) ..................... 0623395

(51) Int. Cl.
*A61M 39/02* (2006.01)

(52) U.S. Cl.
CPC ... *A61M 39/0247* (2013.01); *A61M 2039/025* (2013.01); *A61M 2039/0264* (2013.01);
(Continued)

(58) Field of Classification Search
CPC .......... A61M 2210/0693; A61M 39/02; A61M 39/04; A61M 39/0247; A61M 2039/0282;
(Continued)

(56) References Cited

U.S. PATENT DOCUMENTS 3,452,366 A * 7/1969 Downey ........... A61M 39/0247
604/289
4,013,074 A 3/1977 Siposs
(Continued)

FOREIGN PATENT DOCUMENTS

CN 2684843 Y 3/2005
CN 2834581 Y 11/2006
(Continued)

OTHER PUBLICATIONS

Jun. 17, 2016 Office Action issued in U.S. Appl. No. 13/575,759.
(Continued)

*Primary Examiner* — Emily L Schmidt
(74) *Attorney, Agent, or Firm* — Oliff PLC (57) ABSTRACT

Apparatus for delivering therapeutic agents to the central nervous system of a subject is described. The apparatus includes at least one intracranial catheter and a percutaneous access device. The percutaneous access device includes a body having at least one extracorporeal surface and at least one subcutaneous surface, the body defining at least one port for connection to an implanted intracranial catheter. The port is accessible from the extracorporeal surface of the device, but is provided with a seal such as a rubber bung between the lumen of the port and the extracorporeal surface. The percutaneous access device may have more than two ports and/or a flange. A method of implanting the percutaneous access device is also described.

4 Claims, 9 Drawing Sheets

Related U.S. Application Data continuation of application No. 12/312,584, filed as application No. PCT/GB2007/004438 on Nov. 21, 2007, now Pat. No. 8,974,422.

(52) U.S. Cl.
CPC ............ *A61M 2039/0276* (2013.01); *A61M 2039/0282* (2013.01); *A61M 2039/0285* (2013.01); *A61M 2039/0291* (2013.01); *A61M 2210/0693* (2013.01)

(58) Field of Classification Search
CPC .... A61M 2039/025; A61M 2039/0264; A61N 1/0539
See application file for complete search history.

(56) References Cited

U.S. PATENT DOCUMENTS

| | | | |
|---|---|---|---|
| 4,511,355 A | 4/1985 | Franetzki et al. | |
| 4,578,063 A | 3/1986 | Inman et al. | |
| 4,581,012 A * | 4/1986 | Brown .............. | A61M 39/0247 604/533 |
| 4,634,422 A | 1/1987 | Kantrowitz et al. | |
| 4,692,147 A | 9/1987 | Duggan | |
| 4,695,273 A * | 9/1987 | Brown ................. | A61M 39/10 604/173 |
| 4,705,464 A | 11/1987 | Arimond | |
| 4,772,263 A | 9/1988 | Dorman et al. | |
| 4,790,826 A | 12/1988 | Elftman | |
| 4,822,339 A | 4/1989 | Tran | |
| 4,897,081 A | 1/1990 | Poirier et al. | |
| 4,903,707 A | 2/1990 | Knute et al. | |
| 5,098,397 A | 3/1992 | Svensson et al. | |
| 5,120,313 A | 6/1992 | Elftman | |
| 5,122,114 A | 6/1992 | Miller et al. | |
| 5,171,216 A | 12/1992 | Dasse et al. | |
| 5,221,474 A | 6/1993 | Yokono et al. | |
| 5,318,545 A | 6/1994 | Tucker | |
| 5,352,207 A | 10/1994 | Nussbaum | |
| 5,752,930 A | 5/1998 | Rise et al. | |
| 5,782,645 A | 7/1998 | Stobie et al. | |
| 5,833,655 A | 11/1998 | Freed et al. | |
| 5,836,935 A | 11/1998 | Ashton et al. | |
| 5,906,596 A | 5/1999 | Tallarida | |
| 5,916,200 A | 6/1999 | Eppley et al. | |
| 5,954,687 A | 9/1999 | Baudino | |
| 5,990,382 A | 11/1999 | Fox | |
| 6,018,094 A | 1/2000 | Fox | |
| 6,086,555 A | 7/2000 | Eliasen et al. | |
| 6,134,477 A | 10/2000 | Knuteson | |
| 6,152,933 A | 11/2000 | Werp et al. | |
| 6,347,711 B1 | 2/2002 | Goebel et al. | |
| 6,356,792 B1 | 3/2002 | Errico et al. | |
| 6,454,774 B1 | 9/2002 | Fleckenstein | |
| 6,471,689 B1 | 10/2002 | Joseph et al. | |
| 6,607,504 B2 | 8/2003 | Haarala et al. | |
| 6,609,020 B2 | 8/2003 | Gill | |
| 6,685,674 B2 | 2/2004 | Douglas et al. | |
| 6,758,841 B2 | 7/2004 | Haarala et al. | |
| 6,840,919 B1 | 1/2005 | Hakansson | |
| 6,852,106 B2 | 2/2005 | Watson et al. | |
| 7,331,940 B2 | 2/2008 | Sommerich | |
| 7,604,658 B2 | 10/2009 | Wilson et al. | |
| 7,833,204 B2 | 11/2010 | Picha | |
| 8,323,270 B2 | 12/2012 | Shachar et al. | |
| 8,827,987 B2 | 9/2014 | Fielder et al. | |
| 8,974,422 B2 | 3/2015 | Gill et al. | |
| 9,439,774 B2 | 9/2016 | de Villiers et al. | |
| 10,596,362 B2 | 3/2020 | Fielder et al. | |
| 2002/0133232 A1 | 9/2002 | Ricci et al. | |
| 2003/0004520 A1 | 1/2003 | Haarala et al. | |
| 2003/0023208 A1 | 1/2003 | Osypka et al. | |
| 2003/0120215 A1 | 6/2003 | Bousquet | |
| 2003/0130577 A1 | 7/2003 | Purdy et al. | |
| 2003/0171711 A1 | 9/2003 | Rohr et al. | |
| 2003/0171738 A1 | 9/2003 | Konieczynski et al. | |
| 2004/0034367 A1 | 2/2004 | Malinowski | |
| 2004/0243064 A1 | 12/2004 | Sommerich | |
| 2004/0249361 A1 | 12/2004 | Denoth et al. | |
| 2004/0260361 A1 | 12/2004 | Gibson | |
| 2004/0267238 A1 | 12/2004 | Haarala et al. | |
| 2005/0075624 A1 | 4/2005 | Miesel | |
| 2005/0143800 A1 | 6/2005 | Lando et al. | |
| 2005/0182420 A1 | 8/2005 | Schulte et al. | |
| 2005/0203486 A1 | 9/2005 | Sommerich | |
| 2005/0245887 A1 | 11/2005 | Olsen et al. | |
| 2005/0267591 A1 | 12/2005 | Ricci et al. | |
| 2005/0283203 A1 | 12/2005 | Flaherty et al. | |
| 2006/0122578 A1 | 6/2006 | Lord et al. | |
| 2007/0255262 A1 | 11/2007 | Haase | |
| 2008/0287910 A1 | 11/2008 | Picha | |
| 2009/0030373 A1 | 1/2009 | Gill | |
| 2009/0082758 A1 | 3/2009 | Gill et al. | |
| 2009/0187149 A1 | 7/2009 | Nelson | |
| 2009/0227989 A1 | 9/2009 | Burke et al. | |
| 2010/0042070 A1 | 2/2010 | Gill et al. | |
| 2010/0069892 A1 | 3/2010 | Steinbach et al. | |
| 2010/0145162 A1 | 6/2010 | Devauchelle et al. | |
| 2010/0217236 A1 | 8/2010 | Gill et al. | |
| 2012/0310182 A1 | 12/2012 | Fielder et al. | |
| 2014/0343500 A1 | 11/2014 | Fielder et al. | |
| 2014/0371679 A1 | 12/2014 | Woolley et al. | |

FOREIGN PATENT DOCUMENTS

| | | |
|---|---|---|
| CN | 201088751 Y | 7/2008 |
| CN | 101384286 A | 3/2009 |
| CN | 101400386 A | 4/2009 |
| CN | 101541356 A | 9/2009 |
| DE | 20115120 U1 | 3/2002 |
| DE | 10143820 A1 | 3/2003 |
| EP | 0266243 A1 | 5/1988 |
| EP | 0992257 A1 | 4/2000 |
| EP | 1 426 074 A1 | 6/2004 |
| EP | 1 481 697 A1 | 12/2004 |
| EP | 1576975 A1 | 9/2005 |
| EP | 1704891 B1 | 6/2011 |
| FR | 2690625 A1 | 11/1993 |
| FR | 2750054 A1 | 12/1997 |
| GB | 2389791 A | 12/2003 |
| GB | 2459101 A | 10/2009 |
| JP | S48-5290 A | 1/1973 |
| JP | S62-240069 A | 10/1987 |
| JP | H02-168968 A | 6/1990 |
| JP | H03-126438 A | 5/1991 |
| JP | H03-286776 A | 12/1991 |
| JP | H05-42220 A | 2/1993 |
| JP | H08-141088 A | 6/1996 |
| JP | H11-504231 A | 4/1999 |
| JP | 2001-505115 A | 4/2001 |
| JP | 2001-509063 A | 7/2001 |
| JP | 2004-000495 A | 1/2004 |
| JP | 2006-520656 A | 9/2006 |
| JP | 2006-263470 A | 10/2006 |
| JP | 2006-525827 A | 11/2006 |
| JP | 2009-526589 A | 7/2009 |
| JP | 2009-219889 A | 10/2009 |
| WO | 8907467 A1 | 8/1989 |
| WO | 96/29953 A1 | 10/1996 |
| WO | 9749438 A1 | 12/1997 |
| WO | 98/31417 A2 | 7/1998 |
| WO | 9934754 A1 | 7/1999 |
| WO | 0112158 A1 | 2/2001 |
| WO | 03/077785 A1 | 9/2003 |
| WO | 03077784 A1 | 9/2003 |
| WO | 2004/084768 A2 | 10/2004 |
| WO | 2004105839 A1 | 12/2004 |
| WO | 2007093778 A1 | 8/2007 |
| WO | 2007104953 A1 | 9/2007 |
| WO | 2007104961 A1 | 9/2007 |
| WO | 2008/062173 A1 | 5/2008 |
| WO | 2009047494 A1 | 4/2009 |
| WO | 2009094389 A1 | 7/2009 |

(56) References Cited

FOREIGN PATENT DOCUMENTS

| WO | 2009/103758 A2 | 8/2009 |
|---|---|---|
| WO | 2009096851 A1 | 8/2009 |
| WO | 2009128959 A1 | 10/2009 |
| WO | 2011098769 A1 | 8/2011 |

OTHER PUBLICATIONS

Nov. 17, 2017 Office Action Issued in U.S. Appl. No. 14/445,626.
May 17, 2016 Office Action issued in European Application No. 11 706 900.5.
May 13, 2016 Office Action issued in Chinese Application No. 201210084254.7.
Jul. 20, 2016 Office Action issued in Chinese Patent Application No. 201380051627.3.
Nov. 4, 2016 Office Action Issued in U.S. Appl. No. 14/445,626.
Nov. 4, 2016 Office Action issued in Chinese Patent Application No. 201410772721.4.
Jan. 10, 2018 Office Action issued in Chinese Patent Application No. 201510612697.2.
Oct. 26, 2016 Office Action issued in Application No. 201210084254.7.
Mar. 14, 2017 Office Action Issued in U.S. Appl. No. 13/575,759.
Mar. 15, 2018 Office Action issued in U.S. Appl. No. 13/575,759.
Jan. 30, 2019 Office Action issued in U.S. Appl. No. 14/445,626.
Jun. 15, 2017 Office Action Issued in U.S. Appl. No. 14/445,626.
May 17, 2017 Office Action issued in Indian Patent Application No. 3334/DELNP/2009.
May 24, 2017 Office Action issued in European Patent Application No. 13771208.9.
May 15, 2017 Office Action issued in Japanese Patent Application No. 2015-533703.
Aug. 23, 2017 Office Action Issued In U.S. Appl. No. 13/575,759.
Jun. 8, 2018 Office Action issued in U.S. Appl. No. 14/445,626.
Dec. 6, 2018 Office Action issued in U.S. Appl. No. 13/575,759.
Mar. 14, 2017 Office Action issued in U.S. Appl. No. 14/581,549.
Aug. 28, 2017 Office Action issued in U.S. Appl. No. 14/581,549.
Mar. 3, 2020 Patent Board Decision issued in U.S. Appl. No. 14/581,549.
Oct. 9, 2014 Office Action issued in Japanese Application No. 2012-552463.
Nov. 14, 2014 Office Action issued in Japanese Application No. 2012-552462.
Feb. 25, 2015 Office Action issued in Chinese Application No. 201180009002.1.
Jun. 30, 2011 Written Opinion of International Search Report issued in PCT/GB2011/000183.
Jun. 30, 2011 Written Opinion of International Search Report issued in PCT/GB2011/000182.
U.S. Appl. No. 13/575,759, filed Jul. 27, 2012 in the name of Fielder et al.
May 21, 2010 Search Report issued in Patent Application No. GB1002370.3.
"Linear Incision Technique—Procedure and Clinical Results". BAHA Clinical Review.
N.K.O. & Hoofd-Halsheelkunde, "Bone Anchored Hearing Aids (B.A.H.A.)". http://www.nko.uza.be/prof/baha/index.html. Oct. 11, 2008. 5 pages.
Borenstein, Jeffrey T. "Medicine by Micromachine". IEEE Spectrum. Nov. 2009. Int. pp. 35-39.
Bovo, R. "Simplified technique without skin flap for the bone-anchored hearing aid (BAHA) implant". ACTA Otorhinolaryngologica Italica 2008. 28, pp. 252-255. Ferrara, Italy.
Jul. 25, 2013 Office Action issued in Chinese Patent Application No. 201180009336.9.
Aug. 16, 2013 Office Action issued in Chinese Patent Application No. 201180009002.1.
Mar. 3, 2014 Office Action issued in Chinese Patent Application No. 201180009336.9.
Jun. 23, 2014 Office Action issued in Chinese Patent Application No. 201180009002.1.
Lundgren et al. "Soft-Tissue-Anchored Percutaneous Device for Long-Term Intracorporeal Access." Journal of Investigative Surgery, vol. 2, pp. 17-27.1989.
Fricova et al. "The Implantable Intravenous Ports". Bolest. 2006. pp. 165-172.
Nyman et al. "Soft-Tissue-Anchored Transcutaneous Port for Long-Term Percutaneous Transhepatic Biliary Drainage" CardioVascular and Interventional Radiology vol. 28, pp. 53-59. 2005.
Berntorp et al. "Experience with a new percutaneous port system, Percuseal, for intravenous injection in patients with haemophilia, von Willebrand disease and severe alpha.sub.1-antitrypsin deficiency". Haemophilia, vol. 9, pp. 173-178. 2003.
Germano et al. "Surgical Techniques for Stereotactic Implant of Deep Brain Stimulators". Seminars in Neurosurgery. vol. 12, No. 2, pp. 213-223. 2001.
"Lead Kit for Deep Brain Stimulation". Medtronic Manual, pp. 9-56. 2002.
May 6, 2013 Chinese Office Action issued in Application No. 201210084254.7.
Jul. 6, 2012 Office Action issued in Japanese Patent Application No. 2009-537691.
Mar. 25, 2014 Office Action issued in Chinese Application No. 201210084254.7.
Sep. 20, 2013 Office Action issued in Japanese Application No. 2009-537691.
Dec. 12, 2014 Office Action issued in Canadian Application No. 2,670,164.
Nov. 15, 2014 Office Action issued in Chinese Application No. 201210084254.7.
Oct. 18, 2013 Office Action issued in U.S. Appl. No. 13/575,769.
Feb. 24, 2014 Office Action issued in U.S. Appl. No. 13/575,769.
May 2, 2016 Office Action issued in Japanese Application No. 2015-166782.
U.S. Appl. No. 14/431,133, filed Mar. 25, 2015 in the name of Woolley et al.
May 9, 2014 Office Action issued in U.S. Appl. No. 12/312,584.
Dec. 18, 2013 Office Action issued in U.S. Appl. No. 12/312,584.
Aug. 10, 2011 Office Action issued in U.S. Appl. No. 12/312,584.
Dec. 6, 2010 Office Action issued in U.S. Appl. No. 12/312,584.
Apr. 4, 2008 International Search Report issued in International Patent Application No. PCT/GB2007/004438.
Jun. 30, 2011 International Search Report issued in International Patent Application No. PCT/GB2011/000183.
Jun. 30, 2011 International Search Report issued in International Patent Application No. PCT/GB2011/000182.
Jan. 31, 2014 International Search Report issued in International Patent Application No. PCT/GB2013/052559.
Dec. 31, 2012 Search Report issued in GB Patent Application No. 1217606.01.
Jan. 31, 2014 Written Opinion of International Search Report issued in International Patent Application No. PCT/GB2013/052559.
U.S. Appl. No. 14/445,626, filed Jul. 29, 2014 in the name of Fielder et al.
Apr. 4, 2008 Written Opinion of International Search Report Issued in PCT/GB2007/004438.
Jul. 1, 2015 Office Action issued in Chinese Application No. 201210084254.7.
Jul. 31, 2015 Office Action issued in U.S. Appl. No. 13/575,759.
Jun. 22, 2016 Office Action issued in U.S. Appl. No. 14/431,133.
Dec. 11, 2015 Search Report issued in European Application No. 15 18 1867.
Apr. 26, 2016 Office Action issued In U.S. Appl. No. 14/445,626.
Jan. 18, 2023 Office Action Issued in U.S. Appl. No. 16/826,574.

* cited by examiner

NEUROLOGICAL APPARATUS COMPRISING A PERCUTANEOUS ACCESS DEVICE

This application is a Continuation of application Ser. No. 14/581,549, filed Dec. 23, 2014, which is a Continuation of application Ser. No. 12/312,584, filed May 18, 2009, which is a PCT National Stage of PCT/GB2007/004438 filed Nov. 21, 2007. The disclosures of the prior applications are hereby incorporated by reference herein in their entirety.

BACKGROUND

The invention relates to a percutaneous implant, especially neurological apparatus comprising a percutaneous access device suitable for use with an implanted intracranial catheter.

A percutaneous device is a device which crosses the skin, providing a connection between the interior and exterior of the body. Such devices include dental implants, external hearing aid attachments, artificial limb attachments and semi-permanent catheters. Some percutaneous devices are anchored into bone and some are anchored in soft tissue. All percutaneous devices protrude out of the skin, breaking the barrier that the skin usually provides against infection. Percutaneous devices fail due to a number of reasons, including marsupialisation, in which the epithelium grows down and forms a pocket around the device thereby rejecting the device. More seriously, though, a percutaneous device is a potential site for infection. Accordingly, it is vital that the junction between the skin and the device is able to prevent infection.

The delivery of therapeutic agents to a particular site in the body can pose a number of problems. For example, a patient may have to undergo repeated surgery to access a site to which a therapeutic agent is to be delivered. It is possible in certain areas of the body, such as the brain, to implant a catheter, allowing permanent access to a specific site. Nevertheless, at present, such catheters do not protrude through the skin, and a patient still requires surgery to expose the end of the catheter and administer therapy. It would be particularly desirable to provide a percutaneous port that can be connected to an implanted catheter to allow repeated delivery of a therapeutic agent. As mentioned above, such catheters may be placed in the brain. Delivering therapeutic agents to the nervous system presents a significant challenge.

Delivery via the bloodstream in most cases is extremely limited due to the inability of some therapeutic agents to cross the blood-brain barrier. An alternative approach is to bypass the bloodstream and introduce agents directly into the nervous system via a catheter system. Such catheterisation is a delicate procedure and for any treatment regime that requires intermittent delivery of therapeutic agents over a period of time it is desirable to leave the catheter in place between sessions. It would be of a significant advantage to provide a percutaneous port that would allow repeated access to a permanent or semi-permanent catheter, without the patient having to undergo surgery. If such a port were provided, it would be critical to prevent bacterial ingress into the catheter and hence into the central nervous system (CNS). Prevention of infection via the port and via the junction between the port and the body would be vital to the patient's safety.

Percutaneous devices have been described in the prior art, however, the described devices are generally for use for accessing a patient's blood stream, rather than the CNS. Examples of such devices for accessing a patient's blood stream are described in US2004/0249361, U.S. Pat. Nos. 6,607,504 and 5,098,397.

SUMMARY

According to a first aspect of the invention, apparatus for delivering a therapeutic agent to the central nervous system is provided, the apparatus comprising at least one intracranial catheter and a percutaneous access device, the percutaneous access device comprising a body having at least one extracorporeal surface and at least one subcutaneous surface, the body defining at least one port for connection to an implanted intracranial catheter, the port being accessible from the extracorporeal surface of the device, but being provided with a seal between the lumen of the port and the extracorporeal surface.

The present invention, in the first aspect, thus provides a percutaneous access device connectable to at least one implanted intracranial catheter. The port of the percutaneous access device may be connected directly to the catheter, or may be indirectly connected, via tubing for example. The port is accessible from the extracorporeal side of the body, i.e. the side of the body that is outside the patient's skin when implanted, and extends to a subcutaneous side, i.e. a side of the body that will be positioned internally when implanted, thereby providing percutaneous access, i.e. access to inside a patient's body. Herein the term subcutaneous is used to refer to any part of the percutaneous access device that, in use, is positioned below the upper surface of the skin. The term is used to mean not only parts that are strictly subcutaneous, i.e. below all of the skin, but also parts that are found in the dermis and epidermis of the skin, that is percutaneous parts. The port may be any shape, for example it may have any cross section and may be substantially straight or may include one or more bends. The shape of the port may be determined by the intended use or positioning of the percutaneous access device or by the number of ports comprised by the percutaneous access device.

As indicated above, the percutaneous access device may contain more than one port. In particular, it may contain two or more ports. This provides the significant advantage that one percutaneous access device may be used to pass a therapeutic agent to a number of internally implanted intracranial catheters. Also, two or more agents may be administered to the patient simultaneously or sequentially, via different ports. The ports may be the same shape or different shapes. The ports may extend from the body of the device to form tubing to connect to an implanted device. Alternatively, the port may be connected to tubing or directly to the implanted intracranial catheters.

Neurological apparatus of the present invention provides a fluidic connection between percutaneous ports and implanted intracranial catheters and has various benefits. In particular, apparatus of the present invention provides control over the infusion of agents into the CNS through different catheters. For example, it is likely that drug administration through different catheters would need to be at different infusion rates and at different durations in order to be able to fill the target structure for each catheter with drug, without causing drug leakage into the cerebrospinal fluid or into an adjacent structure. It may also be necessary to use different infusion pressures depending on the type of tissue that the catheter tip is implanted into thereby ensuring tissue cavitation and reflux of infusate along the catheter/brain interface does not occur. It is also possible that different agents will be therapeutic at different concentrations in different parts of the brain, necessitating the delivery of therapies at different concentrations through individual catheters. The apparatus of the present invention thus allows repeated delivery through the individual catheters, that can be tailored to the nature of the progression of the disease process. For example if tumour recurs around a limited number of catheters, focal delivery to the diseased parts of the brain will be necessary, without exposing the rest of the brain to the therapeutic agents, which may have toxic effects.

The body of the percutaneous access device may be any shape. It may, for example, be tubular or cylindrical in shape. Alternatively, the percutaneous access device may be ovoid or elliptical in shape. Additionally, it may be provided with one or more flanges. Where one or more flanges are provided, the flanges may be arranged in relation to the body so that they are substantially parallel to the skin when the device is implanted. The one or more flanges may be any shape, for example they may be annular. The flanges may be positioned on the body so as to help prevent marsupialisation of the device. In that case, a flange is preferably provided around the end of the body that will be positioned internally in use. It is preferred that the one or more flanges are positioned on the body of the device so as to lie under or adjacent the patient's dermis when implanted.

Advantageously, the device comprises a curved flange. For example, the flange may be attached to a central region of the device body and curve downwardly (i.e. away from the skin surface) as it extends outwards. Conveniently, the flange has a peripheral edge region that, when the percutaneous access device is implanted, is substantially parallel to the surface of the skin. Such a peripheral edge region may be seated on the hypodermis of a subject thereby mechanically stabilising the percutaneous access device. In a preferred embodiment, the percutaneous access device may be implanted in the chest region of a subject. Conveniently, the device may be implanted subclavicularly, for example in proximity to the clavicle. In such a region, movement of the hypodermis (and hence the percutaneous access device) may be reduced due to the underlying bone and muscle structure. As described in more detail below, fluid may be routed from the one or more ports of the percutaneous access device to the associated intracranial catheter via one or more lengths of implanted tubing. If multiple ports are provided, the fluid may be routed to multiple catheters via a length of multi-lumen tubing. Advantageously, the flange comprises an aperture, such as a slot or a hole, through which such tubing can pass. This further increases mechanical stabilisation as the flange does not have to rest on such tubing and there is improved seating of the device on the hypodermis.

The body of the device and the at least one flange may be integrally formed, or may be separately formed and then attached together. The body and flange may be made from the same or different materials. The body and/or flange may be made from, for example, a ceramic (e.g. zirconia, glass etc), a polymer (e.g. a thermoplastic such as polycarbonate or PEEK etc), a metal (e.g. Titanium) or any other appropriate material.

At least part of the percutaneous access device (including any flange) may have a surface that encourages cell ingrowth. For example, the surface may be porous. This may be achieved by making at least part of the percutaneous access device from a porous material such as porous titanium, or by coating at least part of the percutaneous access device with a porous material, such as hydroxyapatite or a nano fibrous matrix. At least part of the subcutaneous surface of the body is preferably porous. This helps to reduce the ingress of bacteria or other microbes by encouraging the skin to form a tight junction with the surface of the device.

Where the body is provided with a flange, at least part of the surface of the flange is preferably coated with and/or made from a material that encourages fibrosis, such as a gauze or mesh, particularly made from polyesters such as Dacron, polypropylene, proline and PTFE or a metal such as titanium. Conveniently, the flange is formed from perforated material. Using a material for the flange that encourages fibrosis may allow the percutaneous access device to be inserted without being stitched in place, as the fibrosis holds the device in position. Further coatings may be applied to the flange to promote cell adhesion. The flange may be made from a flexible material so it is able to move with the skin. Conveniently, the flange is rigid to ensure the skin-device interface is immobilised adjacent to the device.

As indicated above the one or more ports are accessible from the extracorporeal side of the body, but are provided with a seal to prevent or reduce the ingress of microbes. Any appropriate seal may be used. In one embodiment, the seal is in the form of a bung, made from, for example, rubber or silicone. Advantageously, the seal comprises an antimicrobial (e.g. antibacterial) material; e.g. the rubber or silicon bung may be silver impregnated. The extracorporeal surface of the body is arranged to allow access to the one or more ports, through or via the seal. For example, the extracorporeal surface may be provided with one or more apertures or may be removable. In use, a therapeutic agent may be introduced to the port by, for example passing a needle through the aperture and through the bung and injecting the agent into the port. The seal may be replaceable (e.g. under appropriate sterile conditions) from the extracorporeal side of the percutaneous access device.

The apparatus may additionally comprise a cap for attachment to the percutaneous access device when the port is not in use, to provide further defence against the ingress of microbes. The cap may be removably attached to the body. It may simply snap fit on to the body or the body and cap may be provided with screw threading to attach the cap to the body. The screw thread could be around the edges of the body and cap, or the body and cap could be provided with a screw portion and a threaded receiving portion. The cap may be made of any appropriate material, such as a plastic. It may have an antimicrobial, especially antibacterial, coating or may be provided with an antimicrobial, especially antibacterial, lining. The cap may be provided with a seal member, to form a substantially airtight seal between the cap and the body. For example, the cap may have a silicone membrane on the side which comes into contact with the body. Such a seal member may contain or be coated with an antimicrobial, particularly an antibacterial, agent. A post operative cap may also be provided to stabilise the percutaneous access device during the post-implantation healing process. The above described caps may be lockable to the percutaneous access device to prevent unauthorised removal (e.g. by the patient).

The apparatus of the present invention is provided with one or more catheters for intracranial implantation. The intracranial catheters thus allow fluid to be delivered to a site within the cranium. Each intracranial catheter may an intrathecal catheter, an intracerebroventricular catheter, an intraparenchymal catheter or an epidural catheter. Preferably, the one or more intracranial catheters include one or more intraparenchymal catheters; e.g. of the type described in WO2003/077785. The catheter may be directly connected to a port of the percutaneous access device or may be indirectly connected via a length of tubing. If multiple ports and catheters are provided, a multi-lumen tube may be used to carry fluid from the percutaneous access device; the separate lumens branching out to provide a route to each catheter. The apparatus may further comprise one or more other devices to be implanted in a patient.

The apparatus may comprise the percutaneous access device and an external (non-implantable) delivery unit. When the percutaneous access device comprises more than one port, it is advantageous to be able to deliver an agent to more than one port at one time. It is obviously important that the correct agent is delivered to each port. A delivery unit for use with the percutaneous access device of the invention is thus provided, the delivery unit and percutaneous access device being arranged to help to ensure that the agents are correctly delivered.

According to the invention, there is provided a delivery unit for use with the percutaneous access device described herein comprising at least one conduit for delivering a fluid agent, the conduit being provided with a male connection portion for insertion into the port of the percutaneous access device such that the conduit and port are in fluid communication. In particular, the delivery unit comprises two or more conduits. The male connection portion may be any appropriate connection portion that can access the port. For example, the male connection portion could be a needle. Such a needle may be of any appropriate shape, for example it could be oblique ended or round ended.

Apparatus for percutaneous delivery of a substance may thus comprise a percutaneous access device according to the invention and a delivery unit according to the invention. The percutaneous access device and delivery unit are preferably shaped such that they fit together in such a way that, when the percutaneous access device comprises more than one port, the male connection portions of the delivery unit always connect with the same ports. In other words, the percutaneous access device and delivery unit can only be fitted together one way. This ensures that each conduit in the delivery unit always delivers fluid to the same port in the percutaneous access device. For example, the percutaneous access device and delivery unit may have shaped surfaces that must mate in order for them to fit together. Alternatively, one may be provided with a projection which fits into an aperture on the other to control their connection. The percutaneous access device and delivery unit may also be provided with a locking member to allow them to be locked together whilst fluid is delivered from the delivery unit to the percutaneous access device. The delivery unit may be provided with one or more pumps to pump fluid into the percutaneous access device. All or some of the delivery unit may be reusable. Conveniently, the parts of the delivery unit between the pump and the connection to the percutaneous access device are disposable (i.e. single use) to reduce the risk of infection.

In addition to providing a percutaneous access device having one or more ports through which fluid can be routed, one or more further connector functions may be provided. For example, the percutaneous access device may provide one or more electrical connections. Advantageously, the one or more ports of the device may themselves be used to transmit electricity or ultrasound energy via the fluid medium.

According to a second aspect of the invention, there is provided a percutaneous access device for use with more than two intracranial catheters, the percutaneous access device comprising a body having at least one extracorporeal surface and at least one subcutaneous surface, the body defining more than two ports for connection to the more than two intracranial catheters, the more than two ports being accessible from the extracorporeal surface of the device, but being provided with a seal between the lumen of each port and the extracorporeal surface. Further preferred features of such a percutaneous access device are described above.

According to a third aspect of the invention, a percutaneous access device for use with an implanted catheter is provided, the percutaneous access device comprising a body having at least one extracorporeal surface and at least one subcutaneous surface, the body defining at least one port for connection to an implanted device, the port being accessible from the extracorporeal surface of the device, but being provided with a seal between the lumen of the port and the extracorporeal surface, wherein a flange extends outwardly from the body of the percutaneous access device, the flange being curved but having a peripheral edge region that, when the percutaneous access device is implanted, lies substantially parallel to the surface of the skin. Advantageously, when implanted, the peripheral edge region of the flange is seated on the hypodermis. Further preferred features of the flange are described above.

According to a fourth aspect of the invention, a method of implanting a percutaneous access device is provided, the percutaneous access device comprising an extracorporeal portion and a subcutaneous portion, the method comprising the steps, in any suitable order, of; (a) making a first incision in the skin of a subject of a size that enables the whole of the percutaneous access device to be passed therethrough, (b) making a second incision in the skin of the subject of a size that allows only the extracorporeal portion to pass therethrough, (c) forming, via the first incision, a subcutaneous pocket under the second incision that is of sufficient size to receive the percutaneous access device, and (d) passing the percutaneous access device through the first incision into the pocket and locating the percutaneous access device within the pocket such that the extracorporeal portion passes through the second incision. Advantageously, the subcutaneous portion of the percutaneous access device comprises a flange extending from a body. The method is advantageously used to implant a percutaneous access device as described herein.

According to a fifth aspect of the invention, a method of delivering therapeutic agents to the nervous system (e.g. CNS) is provided, the method comprising the steps, in any suitable order, of; (i) implanting one or more catheters for fluid delivery to the nervous system of a subject, (ii) implanting a percutaneous access device in the subject, the percutaneous access device comprising a port in fluid communication with the one or more catheters, the port also being accessible from an extracorporeal surface of the percutaneous access device, and (iii) using at least one external pump to deliver a therapeutic agent to the one or more catheters via the percutaneous access device.

Advantageously, step (iii) is performed periodically, the external pump being disconnected from the percutaneous access device when the delivery of therapeutic agents is not required. Conveniently, step (i) comprises implanting a plurality of catheters and step (iii) comprises delivering a therapeutic agent to each catheter wherein the delivery to each catheter is performed using at least one of different infusion rates and different infusion durations. The method is advantageously used with a percutaneous access device as described herein According to a further aspect of the invention, there is provided a percutaneous access device for use with at least one intracranial catheter, comprising a body having at least one extracorporeal surface and at least one subcutaneous surface, the body defining at least one port for connection to an implanted device, the port being accessible from the extracorporeal surface of the device but being provided with a seal between the entry to the lumen of the port and the extracorporeal surface. Further preferred features of such a percutaneous access device are described above.

BRIEF DESCRIPTION OF THE DRAWINGS

The invention will now be described, by way of example only, with reference to the accompanying drawings in which.

DETAILED DESCRIPTION OF EMBODIMENTS

Figure 1:
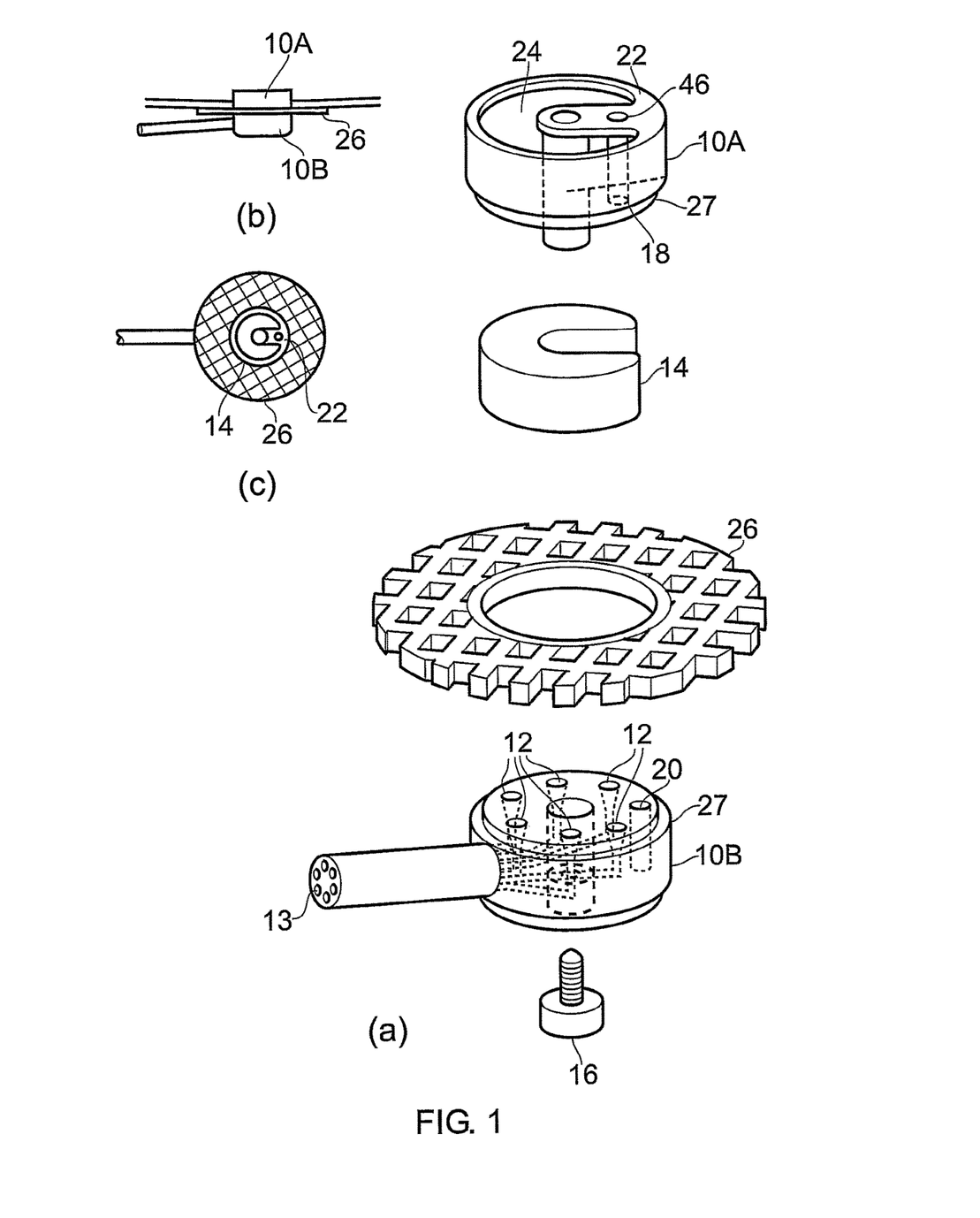
FIG. 1 shows a possible construction of the percutaneous access device of the invention, (a) showing the parts of device separated from one another, (b) showing the device from the side, when in the skin, and (c) showing the device from above.

Referring first to FIG. 1, the percutaneous access device comprises a body. The body may be made from one piece or may have two parts, an upper part 10A and a lower part 10B, which fit together. In the embodiment shown, the lower part of the body, 10B, defines a number of ports, 12. The body may define any number of ports, for example, one port, two ports, three ports or four or more ports. In the embodiment shown, there are six ports. The ports extend into tubing 13, that extends from the side of the body 10 and away from the body. Such tubing may be connected to implanted devices (not shown).

In order to substantially seal the ports 12, to prevent the ingress of microbes, a bung 14 is provided. The bung is positioned on top of the lower part of the body 10B, over the entries to the ports. To hold the bung in place, the upper part of the body 10A, is positioned over it, and fixed to the lower part of the body, via, for example a screw fixing 16. The upper and lower parts of the body and bung are appropriately shaped to allow them to fit together. Advantageously, the upper and lower parts of the body may be provided with guide components, such as a projection 18 and corresponding recess 20 to ensure they are fixed together correctly.

The extracorporeal surface 22 of the upper part of the body is provided with an aperture 24. The aperture is present to allow access to the ports by, for example, injection through the bung.

In order to reduce the need for the percutaneous access device to be stitched in place, it may be provided with a flange 26 made of a material that encourages fibrosis. The flange may be integral with the body or may be made separately and attached to or placed on the body when used. In the embodiment shown in FIG. 1, the body parts 10A and 10B are provided with shoulders 27, forming a groove around the body when the two parts are fixed together. The flange is held in this groove.

Figure 2:
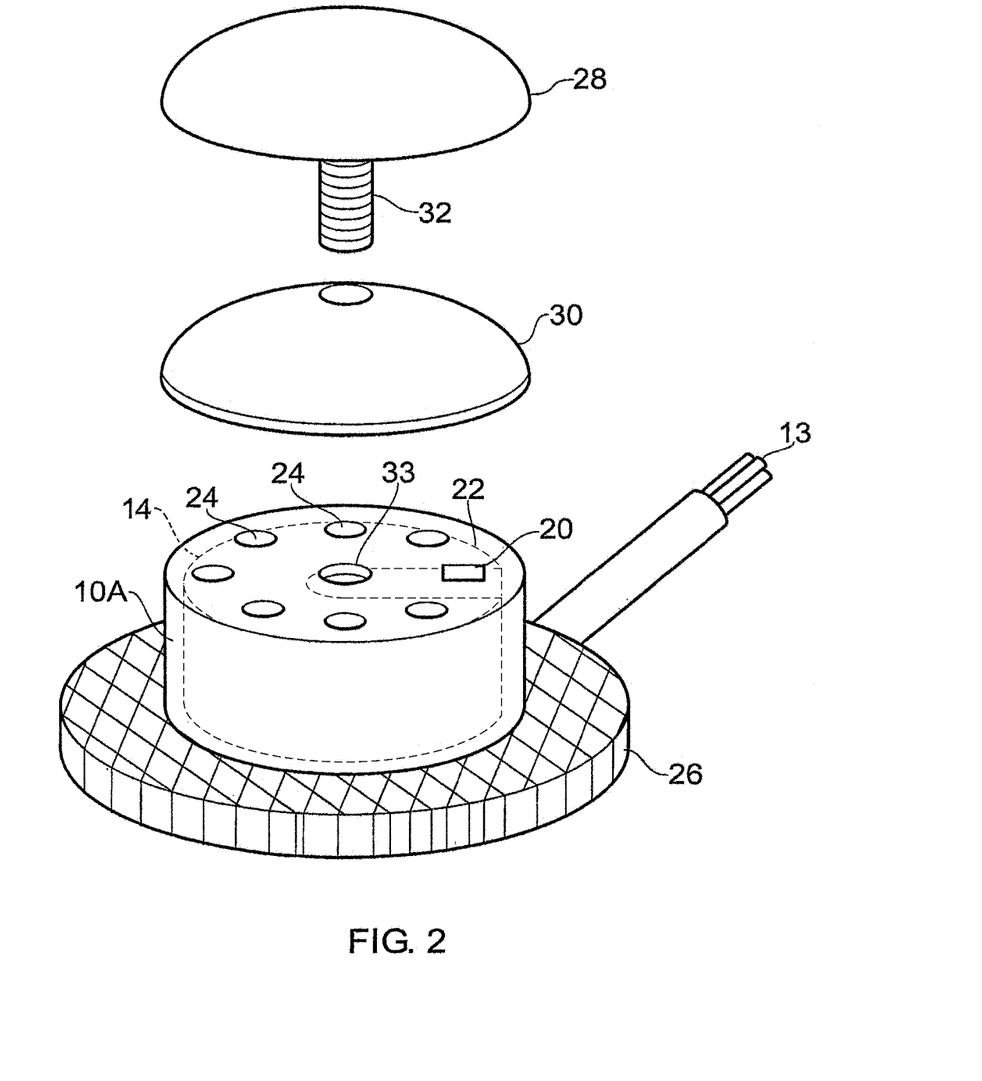
FIG. 2 shows a perspective view of another embodiment of the percutaneous access device and the cap.

Referring to FIG. 2, the body may be provided with a cap 28 for attachment to the body, to assist with preventing ingress of microbes. The cap may have an antimicrobial (e.g. antibacterial) lining 30. The cap may be attached to the body via a screw 32 which fits into a threaded recess 33 in the body. In FIG. 2, the upper part of the body 10A includes a plurality of apertures 24, rather than a single aperture as shown in FIG. 1.

Figure 3:
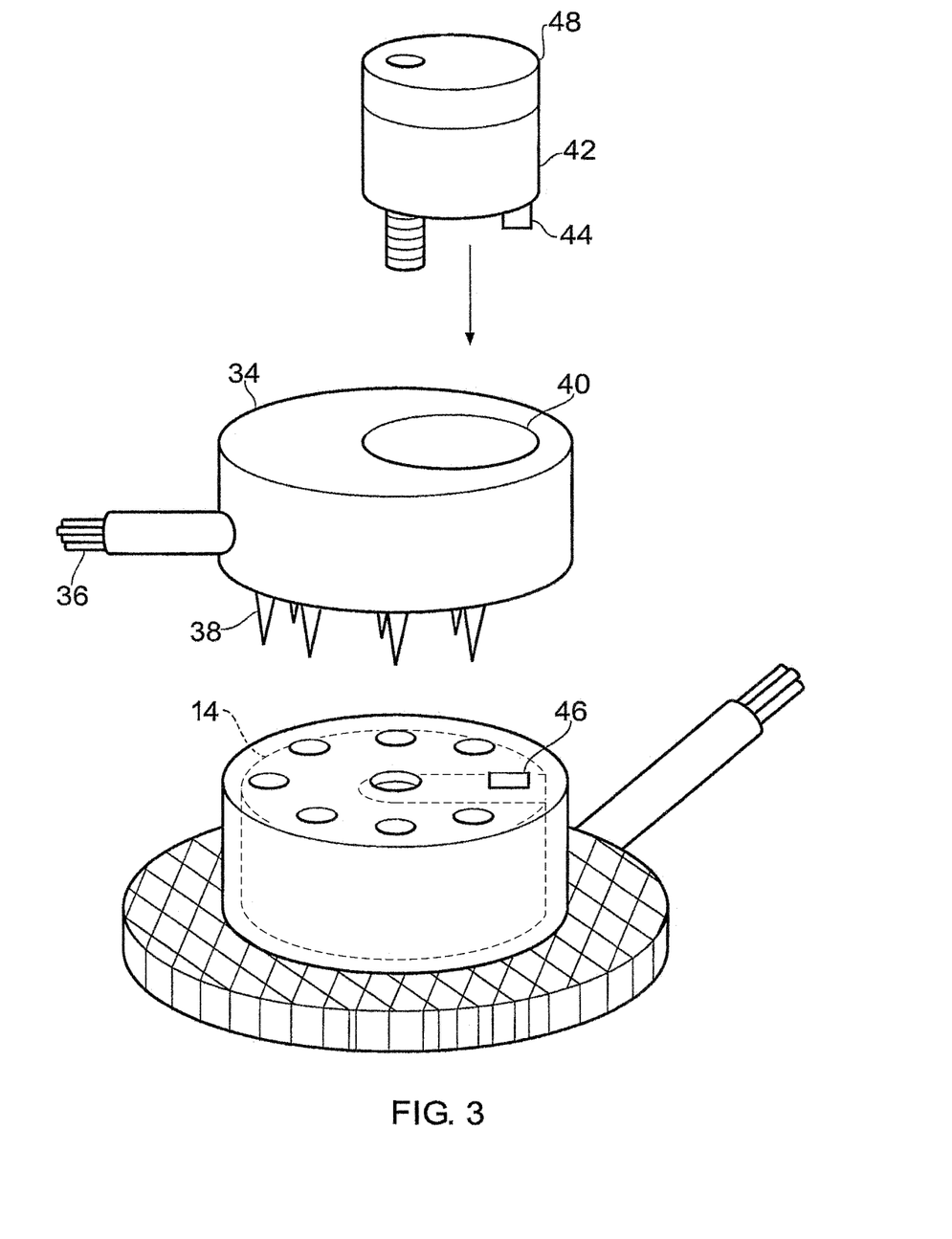
FIG. 3 shows the attachment of one embodiment of the delivery unit to the one embodiment of the percutaneous access device.

In FIG. 3, the delivery unit 34 can be seen. It comprises a number of conduits 36, each having a male connection member 38, such as a needle. In order to ensure the delivery unit is attached correctly to the percutaneous access device, it is provided with an aperture 40. The aperture fits onto a guide member 42 on the percutaneous access device. The guide member 42 may be integral to the body or may be separate from it and simply attachable when the delivery unit is to be used. The guide member may comprise a screw thread and be attachable to the body via the same threaded recess used to attach the cap. The guide member and body may have a projection 44 and recess 46, to position the guide member correctly. The guide member may comprise a locking portion 48, attached to the guide member by, for example, a hinge. In use, the locking member may be moved into a locking position to lock the delivery unit in place.

In use, a cutter is used to cut a hole in the patient's skin, into which the percutaneous access device is introduced. The ports may be attached to the implanted devices, such as catheters. The flange is positioned under the dermis of the skin. The percutaneous access device need not be stitched in place as the flange will encourage fibrosis to hold the percutaneous access device in place. The lower and upper parts of the body may be inserted separately and joined after insertion. Post-operatively, a post-operative cap may be applied whilst the wound heals. The post-operative cap is preferably wider in diameter than the body. Once the wound has healed, the post-operative cap may be removed and the standard cap may be applied.

When a therapeutic agent is to be administered, the cap is removed. The guide member is screwed into place. The delivery unit is placed onto the percutaneous access device, positioned with its aperture over the guide member. The locking member is swivelled to lock the delivery unit in place.

In placing the delivery unit in position, the male connection members will have been inserted into the bung. The male connection members mate with the female entrances to the ports. As a result the conduits and ports are in fluid communication. Therapeutic agents may be pumped from the conduits, through the ports and into the implanted devices.

Figure 4:
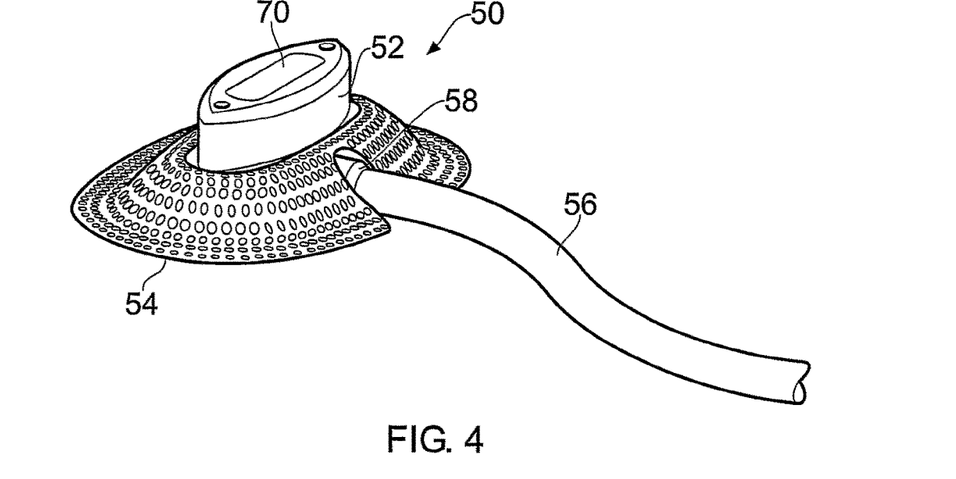
FIG. 4 shows a further possible construction of a percutaneous access device of the invention.
Figure 5:
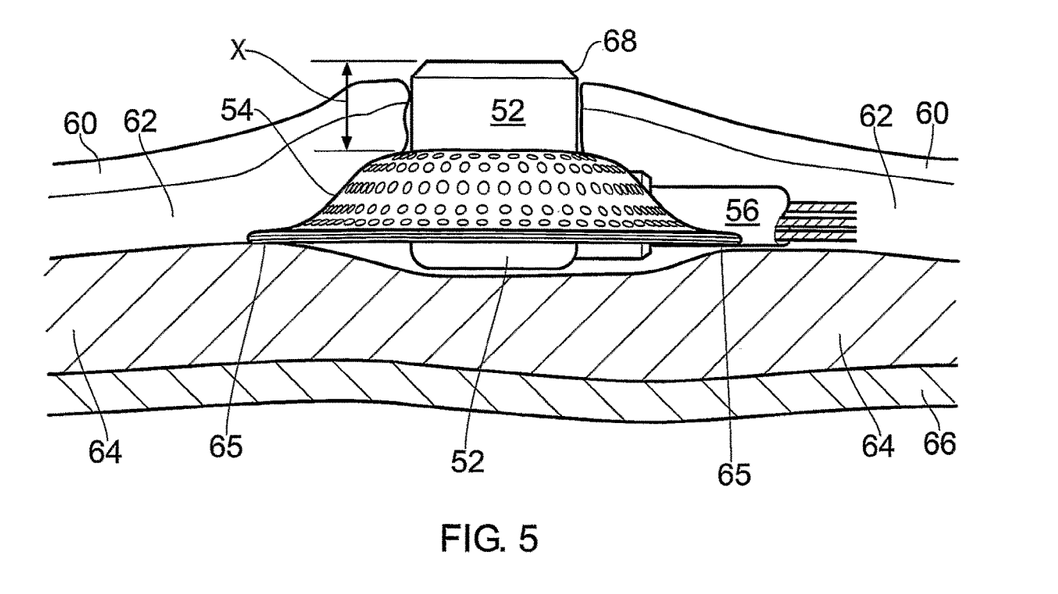
FIG. 5 illustrates the percutaneous access device of FIG. 4 when implanted.

Referring to FIGS. 4 and 5, a further percutaneous access device 50 in accordance with the present invention is illustrated. As shown in FIG. 4, the device 50 comprises a body 52 having an elliptical profile and a surrounding perforated flange 54. The flange 54 curves downwardly from where it is attached to the body but has a peripheral edge that is arranged to be, when the device is implanted in a subject, substantially parallel to the surface of the skin. A tube 56 comprising multiple lumens exits the device 50 through a slot 58 formed in the flange 54.

In FIG. 5, the percutaneous access device 50 is shown when implanted in a subject. The subject's skin comprises an outer epidermis layer 60, under which are located a dermis layer 62 and a hypodermis layer 64. Hard or firm tissue 66, such as muscle and/or bone, lies under the hypodermis layer 64. The peripheral edge 65 of the flange is designed to contact and rest on the hypodermis layer 64 whilst the upper part of the body 52 protrudes through the epidermis and dermis layers to provide an extracorporeal surface 68 comprising an aperture 70. It should be noted that the flange curves away from the body 52 but is substantially parallel to the surface of the skin at its periphery; this ensures that the outermost or peripheral edge of the flange does not "dig in" to the underlying soft tissues of the hypodermis. The height of the body 52 of the device above the level of the flange 54 (marked as distance "x" in FIG. 5) is slightly greater than the patient's skin (epidermis and dermis) thickness. This reduces the chances that the skin will heal over the top of the access device after implantation.

The flange 54 stabilises the percutaneous access device 50 at its periphery. In particular, the outermost edge of the flange 54 is approximately flush with the underside of the device body 52, thereby stabilising the device 50 over a wide footprint on the underlying soft tissues (e.g. on the hypodermis 64). If the device 50 is implanted over the rib cage as described in more detail below, it is further stabilised by the bone and muscle structure 66 below the hypodermis. In this manner, the access device is resistant to tipping or tilting during the day to day activities of the patient and particularly when a suitable delivery unit (e.g. in the form of an administration connector) is attached for delivery of an agent.

Furthermore, as described above, the tubing 56 exits the percutaneous access device through a slot in the flange without having to pass under the outer edge of the flange. This ensures that the tubing 56 remains below the dermis and improves the seating of the access device on the underlying tissues. The provision of the slot 58 thus also helps to prevent tipping of the access device and improves patient comfort. The percutaneous access device 50 is thus particularly suited to implantation where there is little depth of underlying soft tissues. This should be contrasted to prior art devices where the tubing exits the access device from the underside of the device body, thereby making the device liable to tipping and/or causing tension to be applied to the device-skin interface. Although a slotted flange is shown, the same advantages could be achieved via a hole in the flange or by allowing the tube to exit the port body outside the flange perimeter. It would also be possible to form the flange over the path of the tubing.

The flange 54 is perforated to promote bio-integration. In the present example, such bio-integration is achieved by cell adhesion to the flange surface and also fibrosis in-growth through the perforations of the flange during the healing period after surgical implantation. Bio-integration of the flange thus helps to anchor the device at the implanted location, and also reduces the likelihood of infection around the device-skin interface.

The flange may carry one or more coatings to stimulate cell attachment and proliferation across the flange's surface. Suitable coatings include, but are not limited to, a Calcium Phosphate based coating (e.g. Hydroxyapatite or Fluorapatite) or Siloxane. To aid cell adhesion, the surface of the flange may also be roughened. Surface roughening may be provided by, for example, coating the flange in a biocompatible metal powder (most preferably titanium), generating the flange by direct metal laser sintering (this can also be used to generate porosity through the entire flange thickness), chemical etching the surface of the flange to generate texture and/or mechanical abrasion or blasting (vapour or bead) of the material forming the flange surface. The surface chemistry of the flange can also be modified to generate a surface (e.g. that is more hydrophilic or hydrophobic as appropriate) which promotes cell adhesion. Chemical functional groups can also or alternatively be added to the surface of the flange which attract cells (e.g. fibroblasts) that are key to successful biointegration. Siloxanes with engineered functional groups can be used to achieve this.

Figure 6:
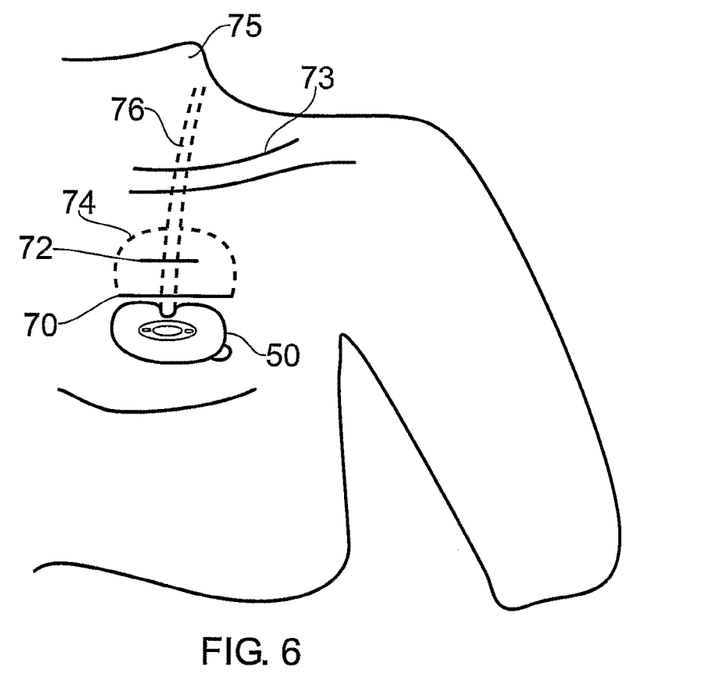
FIG. 6 shows the incisions required to implant the device of FIG. 4.
Figure 7:
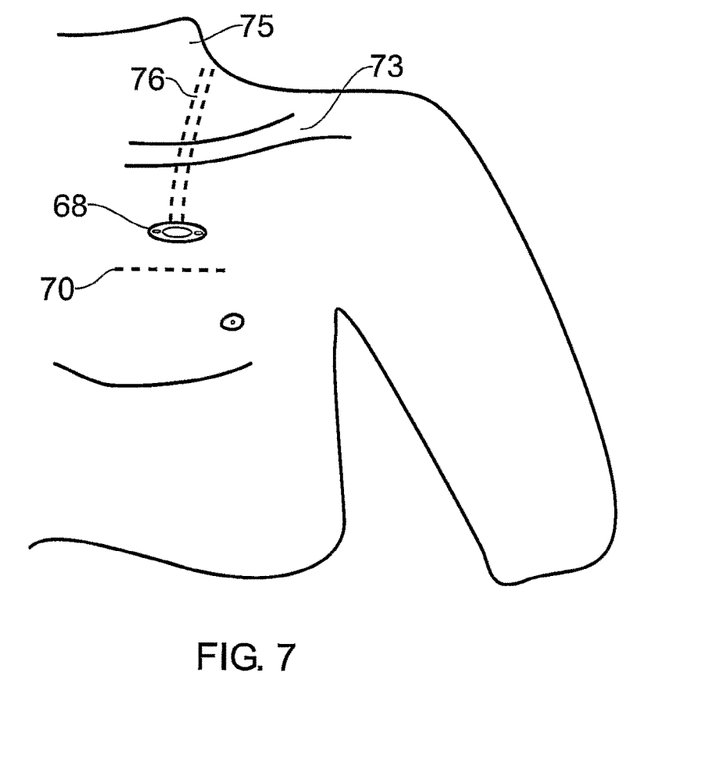
FIG. 7 is an external view of the device of FIG. 4 when implanted.
Figure 8:
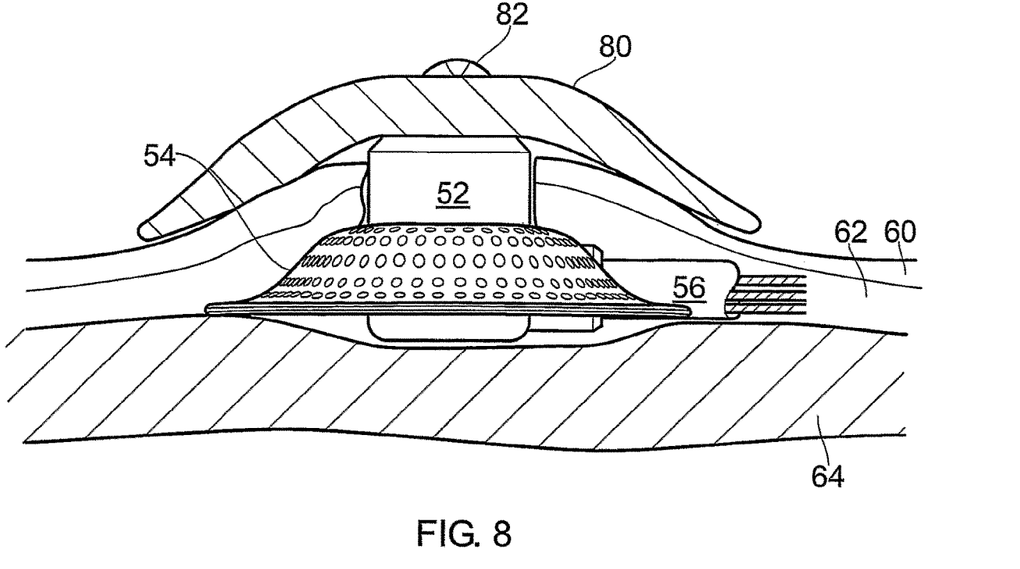
FIG. 8 shows a healing cap attached to the percutaneous access device shown in FIG. 4.

Referring to FIGS. 6 to 8, a technique for implanting the above described percutaneous access device 50 will be described.

As shown in FIG. 6, the implantation method firstly involves cutting two slits 70 and 72 through the skin on the patient's chest below the clavicle 73 and forming a subcutaneous "pocket" 74 between the two incisions. The first incision 70 is big enough to allow the access device 50 to be inserted under the skin and into the pocket. The second incision 72 is shorter than the first but is big enough to allow only the protruding aspect of the access device (i.e. the extracorporeal surface) to be pushed therethrough. A subcutaneous route is then tunnelled from the top of the patient's head, along the neck 75, to the pocket 74. The multi-lumen tubing 76 to be connected to the access device 50 is attached to the tunnelling tool's "drawstring" and pulled under the patient's skin. The access device 50 is then pulled under the skin and finally seated through the short incision 72 in the patient's chest as shown on FIG. 7. The long incision 70 can then be sutured closed.

As illustrated in FIG. 8, when the patient has been adequately sutured and cleaned, a post operative (healing) cap 80 can be placed on the device to ensure that the device does not slip back in to the subcutaneous pocket. An attachment device 82 for holding the post operative cap 80 in place is also provided. The post operative cap ensures the skin lies correctly over the flange 54 and also encourages rapid bio-integration. The post operative cap 80 holds the skin against the flange whilst avoiding over-compression, which may cause necrosis. The post operative cap 80 may also comprise a compressive anti-bacterial element that provides a seal against the outer surface of the septum and thus provides further antimicrobial (e.g. antibacterial) protection.

Figure 9:
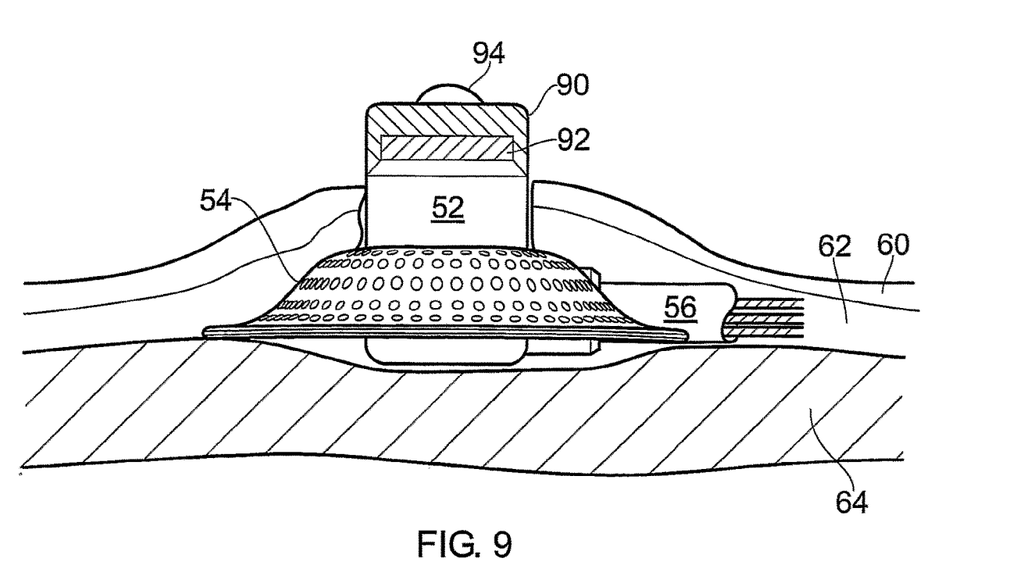
FIG. 9 shows cap attached to the percutaneous access device of FIG. 4.

FIG. 9 illustrates a normal (post-healing) or security cap 90 that may be fitted to the external aspect of the access device 50 after the wound has healed. The security cap 90 is smaller than the healing cap 80 shown in FIG. 8 and is therefore less intrusive to patients during their day-to-day activities. Such a smaller cap also provides access to the skin-device interface to allow cleaning. The security cap 90 may also comprise a compressive anti-bacterial element 92 that provides a seal against the outer surface of the septum and thus provides further antimicrobial (e.g. antibacterial) protection. An attachment device 94 secures the cap in place. Although by no means essential, removal of the security cap may require a key or specialised release member to prevent improper removal (e.g. by the patient).

Figure 10:
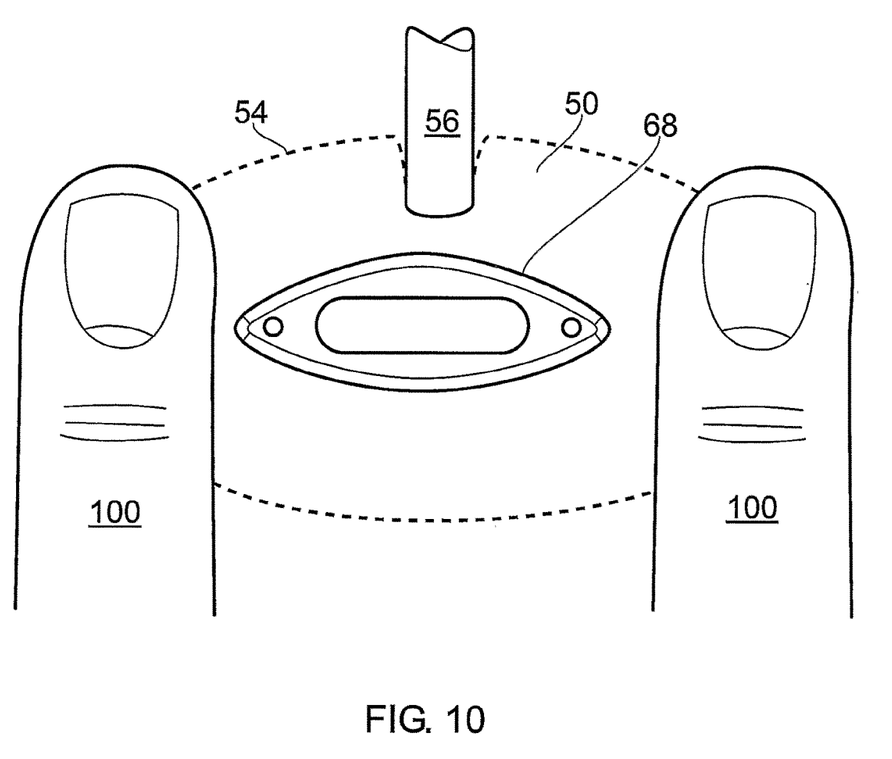
FIG. 10 illustrates how the device of FIG. 4 can be held in place when being connected to an associated delivery unit.

Referring to FIG. 10, a top view of an implanted percutaneous access device 50 is illustrated. The solid lines show the extracorporeal surface 68 of the device that protrudes from the surface of the skin whilst the dashed lines illustrate the subcutaneously implanted parts of the access device (e.g. the flange 54). As described above, the flange 54 varies in height from being at an elevation above the tubing at its inner most aspect, down to the level of the base of the body at its outermost (peripheral) aspect. This variation in flange height is over approximately one finger width and the profile of the flange is designed to be as gentle as possible to minimise aesthetic impact on the patient and tension on the skin. The overall width of the flange thus allows a clinician to stabilise the access device during connection to the delivery unit by placing a finger 100 on the surface of the skin on each side of the protruding port body and applying light pressure.

Figure 11:
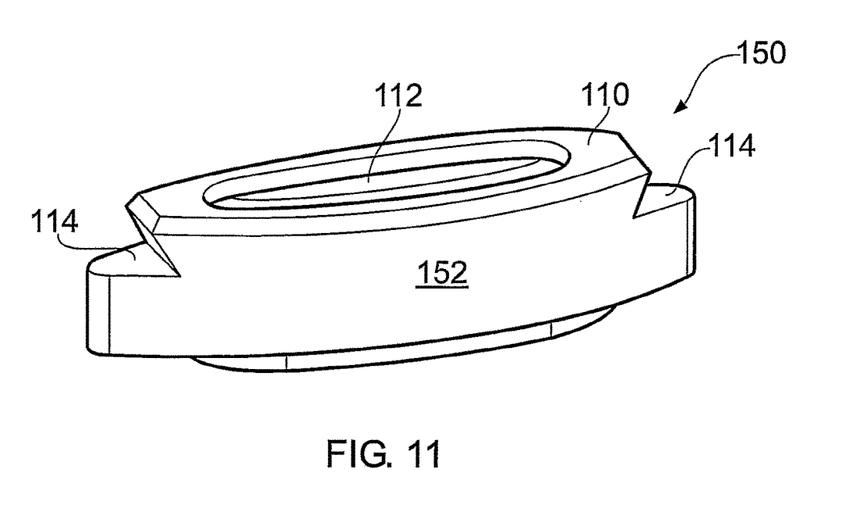
FIG. 11 is a perspective view of the upper elements of a further percutaneous access device of the present invention.
Figure 12:
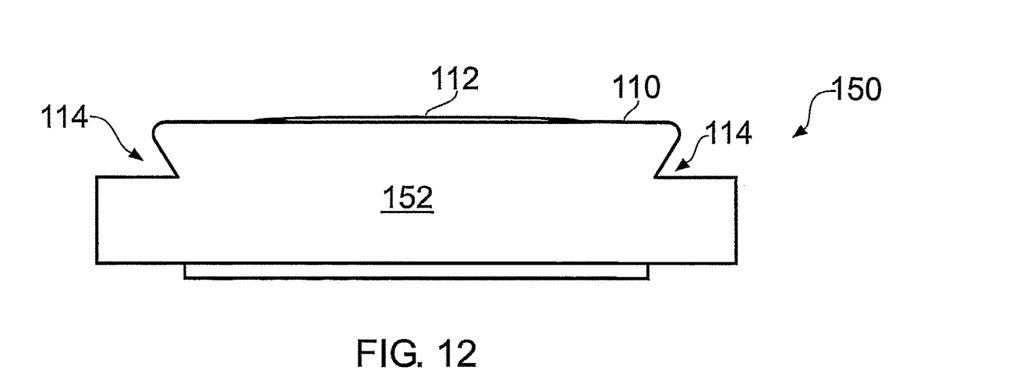
FIG. 12 shows a side view of the device of FIG. 11, FIG. 13 show a sectional view through the device of FIG. 11 and an associated delivery unit.
Figure 13:
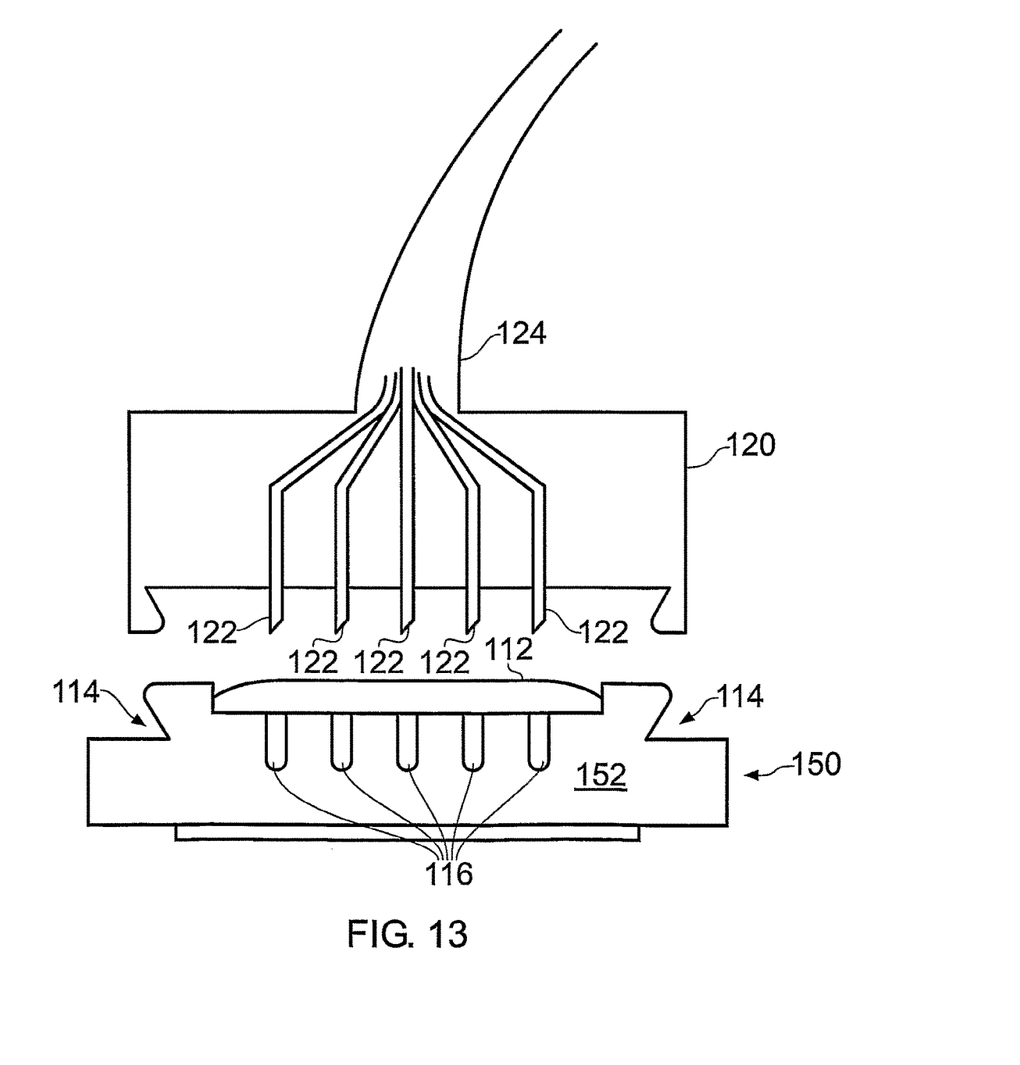

Referring to FIGS. 11 to 13, various views of a further percutaneous access device 150 of the present invention are shown.

FIG. 11 shows a perspective view of the body 152 of the percutaneous access device 150. For clarity, the flange, and other elements of the device below the flange are omitted from the drawing. The device 150 has a upper flat (extracorporeal) surface 110 that comprises a central recess in which a septum 112 is located. Recesses 114 formed at the edge of the body 152 are provided for mating with a delivery unit or cap as described in more detail below.

FIG. 12 shows a side view of the device 150 illustrated in FIG. 11. From FIG. 12 it can be seen how the septum seal 112 is substantially flush with the upper surface 110. This allows the septum seal 112 to be easily accessed for cleaning.

The septum 112 of the access device is provided to prevent infection occurring along the inner lumen of the therapy delivery system. The material used for the septum may thus have anti-microbial (e.g. anti-bacterial) agent properties; for example, the septum may be compounded with silver. Providing such a seal helps to ensure that the fluidic pathways of the device remain bacteria free which, as explained above, is important for neurological applications because the brain has an attenuated immune system and therefore any infection that occurs will present a serious risk to the patient's health. A filter (e.g. an antimicrobial filter) may also be included below the septum to further reduce the chances of infection occurring along the inner lumen of the delivery system.

Referring to FIG. 13, a cross-sectional view through the percutaneous access device 150 and the connector 120 of an associated delivery are shown.

The percutaneous access device 150 comprises channels or conduits 116 that separately run through the body and each provide a port connected to the lumen of an implantable multi-lumen tube. In this example, five channels 116 through the access device 150 provide five ports connectable to implanted devices, such as intracranial catheters or the like. The fluid channels 116 of the ports are isolated from one another. The top of each channel 116 terminates at the septum 112 which is accessible from the extracorporeal surface of the device body 152.

An external delivery unit comprising a connector 120 can be attached to the percutaneous access device 150 when fluid delivery is required. The connector 120 is shaped so as to mate with the percutaneous access device 150. Preferably, it is shaped so as to fit in only one orientation on the percutaneous access device, to minimise the risk of connection errors. The connector also comprises a plurality of needles 122 that, when mated with the access device 150, pass though the septum seal 112 allowing fluid communication to be established between each needle 122 and a respective channel 116 of the access device. Each needle 122 can be connected to the lumen of a tube 124 which may in turn be connected to an external drug delivery pump. In this manner, separate fluidic connections are provided from a pump to an intracranial catheter through the percutaneous access device 150.

Although the external connector 120 described above comprises a plurality of needles that penetrate the septum, it should be noted that "needle-less" connectors may alternatively be used in combination with a septum seal. For example, a connector could be provided that includes truncated needles or protrusions that are arranged to mate with pre-formed slits in the septum. Mating causes the slits in the septum to open thereby allowing fluid to be passed through the septum although no needle is actually passed through the septum. The skilled person would be aware of the various septum based fluid connector systems that could be employed.

Figure 14:
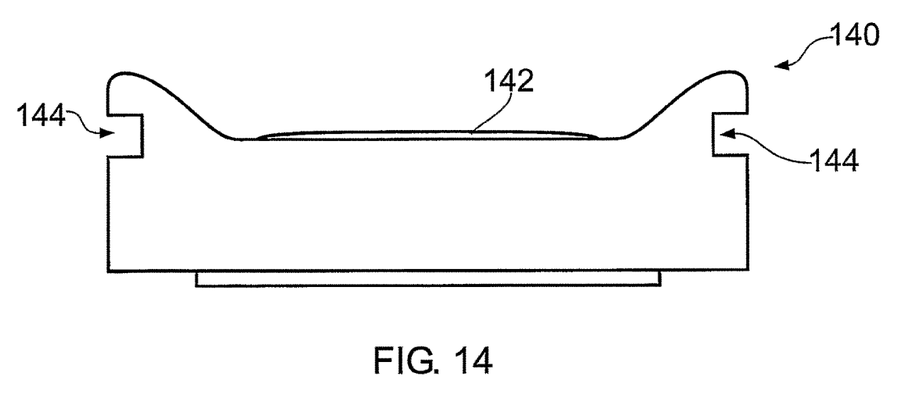
FIG. 14 shows the upper elements of a further percutaneous access device of the present invention.
Figure 15:
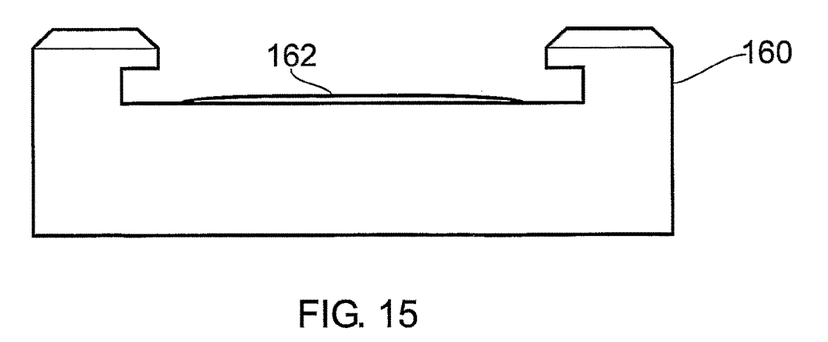
FIG. 15 shows the upper elements of a still further percutaneous access device of the present invention.

Referring to FIGS. 14 and 15, variants of the above described percutaneous access devices are illustrated.

FIG. 14 illustrates a percutaneous access device 140 having a septum 142. The septum 142 is located within a shallow a recess formed in the body of the device 140. A groove 144 extending around the periphery of the body of the device, or in one or more specific locations around the periphery of the body of the device, allows an associated connector or cap to be snapped into engagement with the device 140.

FIG. 15 illustrates a further percutaneous access device 160 having a septum 162 located within an externally accessible cavity. In this example, a groove 164 is formed on the internal wall of the cavity to allow releasable engagement with an associated connector or cap.

The protruding aspect or extracorporeal surface of the device is preferably elliptical or "canoe-shaped" as described with reference to FIGS. 4 to 15 above to allow for neat slit closure around the device, without the need for skin removal. However, the access device could be any shape; for example, it could be circular as described with reference to FIGS. 1 to 3 above. A skilled person would also be aware of the numerous design variants that could be provided.

What is claimed is:

1. A method of delivering a therapeutic agent to a central nervous system of a subject that has a percutaneous access device and at least two intracranial catheters implanted therein, the percutaneous access device comprising a body having at least one extracorporeal surface and at least one subcutaneous surface, the body defining at least two ports for connection to at least two intracranial catheters, each port (i) being accessible from the extracorporeal surface of the device and including a seal between a lumen of the port and the extracorporeal surface, and (ii) separately passing through the body such that each intracranial catheter is separately accessible from the extracorporeal surface of the device, the method comprising:

a step of (i) attaching a delivery unit to the percutaneous access device, the delivery unit comprising at least two conduits for delivering a fluid agent, each conduit being provided with a male connection portion configured to be inserted into a respective one of the ports of the percutaneous access device such that the at least two conduits and the at least two ports are in fluid communication.

2. A method according to claim 1, further comprising a step of (ii) delivering the fluid agent to the central nervous system of the subject using at least one external pump via the at least two intracranial catheters, the percutaneous access device, and the delivery unit.

3. A method according to claim 2, further comprising a step of (iii) disconnecting the delivery unit from the percutaneous access device.

4. A method according to claim 3, wherein steps (i), (ii) and (iii) are performed periodically, and the external pump is disconnected from the percutaneous access device when delivery of the therapeutic agent is not required.

\* \* \* \* \*